(12) United States Patent
Kushida et al.

(10) Patent No.: US 11,248,249 B2
(45) Date of Patent: Feb. 15, 2022

(54) METHOD FOR DETERMINING WHETHER OR NOT SAMPLE CONTAINS CERCOSPORA FUNGUS OR PSEUDOCERCOSPORA FUNGUS

(71) Applicant: Panasonic Intellectual Property Management Co., Ltd., Osaka (JP)

(72) Inventors: Yuki Kushida, Kyoto (JP); Yosifumi Kariatumari, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 119 days.

(21) Appl. No.: 16/561,028

(22) Filed: Sep. 5, 2019

(65) Prior Publication Data
US 2019/0390244 A1 Dec. 26, 2019

Related U.S. Application Data

(63) Continuation of application No. PCT/JP2018/015789, filed on Apr. 17, 2018.

(30) Foreign Application Priority Data

May 12, 2017 (JP) .............................. JP2017-095251

(51) Int. Cl.
| | | |
|---|---|---|
| *C12Q 1/04* | (2006.01) | |
| *G01N 21/31* | (2006.01) | |
| *G01N 21/17* | (2006.01) | |
| *G01N 21/78* | (2006.01) | |
| *C12Q 1/02* | (2006.01) | |
| *C12Q 1/00* | (2006.01) | |

(52) U.S. Cl.
CPC ................ *C12Q 1/04* (2013.01); *C12Q 1/00* (2013.01); *C12Q 1/02* (2013.01); *G01N 21/17* (2013.01); *G01N 21/3151* (2013.01); *G01N 21/78* (2013.01)

(58) Field of Classification Search
CPC .... G01N 21/3151; G01N 21/17; G01N 21/78; C12Q 1/04; C12Q 1/02; C12Q 1/00
See application file for complete search history.

(56) References Cited

PUBLICATIONS

Held, P., 2009. An absorbance-based cytotoxicity assay using high absorptivity, water-soluble tetrazolium salts. Application Note. BioTek Instruments, Inc. PDF provided) (Year: 2009).*
Huang, X., et al. 2005. Gold nanoparticles: Catalyst for the oxidation of NADH to NAD+. Journal of photochemistry and photobiology B: biology, 81(2), pp. 76-83. (Year: 2005).*
Präbst K. et al. 2017. Basic Colorimetric Proliferation Assays: MTT, WST, and Resazurin. In: Gilbert D., Friedrich O. (eds) Cell Viability Assays. Methods in Molecular Biology, vol. 1601. Humana Press, New York, NY. (Year: 2017).*
Rawson F. et al. 2014. Electrochemical detection of intracellular and cell membrane redox systems in *Saccharomyces cerevisiae*. Scientific reports, 4(1), pp. 1-9. (Year: 2014).*
Sigma-Aldrich product information sheet. 2015. Protein Quantification Kit 77371. PDF provided (Year: 2015).*
International Search Report of PCT application No. PCT/JP2018/015789 dated Jul. 24, 2018.
Maria Gabriela Latorre Rapela et al., "Early Detection of *Cercospora* Species in Soybean Plants: Immunologic and Molecular Methods", American Journal of Plant Sciences, 2015, 6, 2939-2948, Nov. 25, 2015.

* cited by examiner

*Primary Examiner* — Allison M Fox
*Assistant Examiner* — Qing Xu
(74) *Attorney, Agent, or Firm* — McDermott Will and Emery LLP

(57) ABSTRACT

The present invention provides a method for determining whether or not a sample contains at least one of Cercospora fungus and Pseudocercospora fungus. In the method, first, the sample is added an aqueous solution containing N,N,N', N'-Tetramethyl-1,4-phenylenediamine and 5-(2,4-disulfophenyl)-3-(2-methoxy-4-nitrophenyl)-2-(4-nitrophenyl)-2H-tetrazolium to provide a mixture. The aqueous solution has a pH of not less than 5.1 and not more than 6.5. Then, the mixture is irradiated with light having a wavelength of 400 to 500 nanometers to measure a first absorbance Ay of the mixture, and the mixture is irradiated with light having a wavelength of 500 to 800 nanometers to measure a second absorbance Ax of the mixture. If the value of Ay/Ax is not less than 1.5 or the mixture is orangey, it is determined that the sample contains at least one of Cercospora fungus and Pseudocercospora fungus.

8 Claims, No Drawings

METHOD FOR DETERMINING WHETHER OR NOT SAMPLE CONTAINS CERCOSPORA FUNGUS OR PSEUDOCERCOSPORA FUNGUS

BACKGROUND

1. Technical Field

The present invention relates to a method for determining whether or not a sample contains Cercospora fungus or Pseudocercospora fungus.

2. Description of the Related Art

Cercospora fungus causes leaf spot. Non-patent Literature 1 discloses a method for quickly detecting Cercospora fungus contained in soybean plants immunologically and molecularly.

CITATION LIST

Non-Patent Literature

Non-patent Literature 1: Maria Gabriela Latorre Rapela et. al., "Early Detection of Cercospora Species in Soybean Plants: Immunologic and Molecular Methods", American Journal of Plant Sciences, 2015, 6, 2939-2948

SUMMARY

An object of the present invention is to provide a novel method for determining whether or not a sample contains Cercospora fungus or Pseudocercospora fungus.

The present invention provides a method for determining whether or not a sample contains at least one of Cercospora fungus and Pseudocercospora fungus, the method comprising:

(a) adding the sample to an aqueous solution containing N,N,N',N-Tetramethyl-1,4-phenylenediamine and 5-(2,4-disulfophenyl)-3-(2-methoxy-4-nitrophenyl)-2-(4-nitrophenyl)-2H-tetrazolium to provide a mixture;

wherein the aqueous solution has a pH of not less than 5.1 and not more than 6.5;

(b) irradiating the mixture with light having a wavelength of not less than 400 nanometers and not more than 500 nanometers to measure a first absorbance Ay of the mixture;

(c) irradiating the mixture with light having a wavelength of more than 500 nanometers and not more than 800 nanometers to measure a second absorbance Ax of the mixture; and (d) determining that the sample contains at least one of Cercospora fungus and Pseudocercospora fungus, if the following mathematical formula (I) is satisfied.

$$Ay/Ax \geq 1.5 \quad (I)$$

In place of the steps (b)-(d), the present invention comprises:

(e) determining that the sample contains at least one of Cercospora fungus and Pseudocercospora fungus, if the mixture is orangey.

The present invention provides a novel method for determining whether or not a sample contains Cercospora fungus or Pseudocercospora fungus.

DETAILED DESCRIPTION OF THE EMBODIMENTS

Hereinafter, the embodiments of the present invention will be described.

First Embodiment

The method according to the first embodiment comprises the following four steps (a)-(d).

(Step (a))

In the step (a), a sample is added to an aqueous solution containing N,N,N',N'-Tetramethyl-1,4-phenylenediamine (hereinafter, referred to as "TMPD") and a compound represented by the following chemical formula (I) to prepare a mixture. Hereinafter, the compound represented by the following chemical formula (I) is referred to as "WST-8".

[Chem. 1]

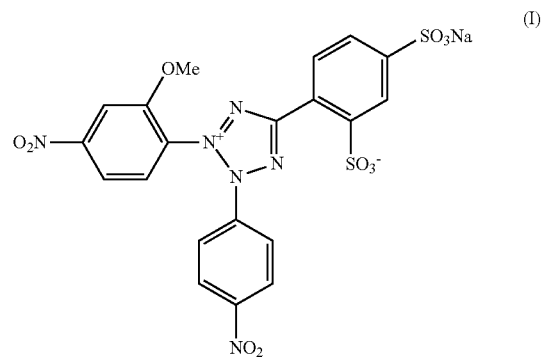

TMPD is commercially available as N,N,N',N'-Tetramethyl-1,4-phenylenediamine Dihydrochloride (CAS No: 637-01-4). WST-8 is commercially available as 5-(2,4-disulfophenyl)-3-(2-methoxy-4-nitrophenyl)-2-(4-nitrophenyl)-2H-tetrazolium, inner salt, monosodium salt (CAS No: 193149-74-5).

The aqueous solution has a pH of not less than 5.1 and not more than 6.5. In case where the aqueous solution has a pH less than 5.1, it is impossible to detect Cercospora fungus and Pseudocercospora fungus. In more detail, although the sample contains at least one of Cercospora fungus and Pseudocercospora fungus, the erroneous conclusion that sample does not contain either Cercospora fungus or Pseudocercospora fungus is led in the step (d) which will be described later. See the comparative example 2 which will be described later.

Also in case where the aqueous solution contains a pH more than 6.5, it is impossible to detect Cercospora fungus and Pseudocercospora fungus. In more detail, although the sample does not contain either Cercospora fungus or Pseudocercospora fungus, the erroneous conclusion that sample contains Cercospora fungus or Pseudocercospora fungus is led in the step (d) which will be described later. See the comparative example 19 which will be described later.

Therefore, the aqueous solution has a pH of not less than 5.1 and not more than 6.5.

The present invention is characterized by that Cercospora fungus or Pseudocercospora fungus is detected because of the combination of TMPD and WST-8 under the proper pH condition (i.e., not less than 5.1 and not more than 6.5). Lack of one of TMPD and WST-8 leads failure of the detection of Cercospora fungus or Pseudocercospora fungus.

It is desirable that the mixture is left at rest at a room temperature for one or more days.

(Step (b))

In the step (b), the mixture provided in the step (a) is irradiated with light having a wavelength of not less than 400 nanometers and not more than 500 nanometers to measure a first absorbance Ay of the mixture. As one example, the mixture may be irradiated with light having a wavelength of 460 nanometers to measure a first absorbance Ay of the mixture.

(Step (c))

In the step (c), the mixture provided in the step (a) is irradiated with light having a wavelength of more than 500 nanometers and not more than 800 nanometers to measure a second absorbance Ax of the mixture. As one example, the mixture may be irradiated with light having a wavelength of 610 nanometers to measure a second absorbance Ax of the mixture.

The order of the step (b) and the step (c) is not limited. In other words, the step (b) may be performed first and then the step (c) may be performed. Alternatively, the step (c) may be performed first and then the step (b) may be performed.

(Step (d))

In the step (d), it is determined that the sample contains at least one of Cercospora fungus and Pseudocercospora fungus, if the following mathematical formula (I) is satisfied.

$$Ay/Ax \geq 1.5 \qquad (I)$$

As is clear from the inventive examples which will be described later, if the mixture contains at least one of Cercospora fungus and Pseudocercospora fungus, the value of Ay/Ax is not less than 1.5. On the other hand, if the mixture does not contain either Cercospora fungus or Pseudocercospora fungus, the value of Ay/Ax is less than 1.5.

In other words, if the mixture contains all of TMPD, WST-8, and at least one of Cercospora fungus and Pseudocercospora fungus, light having a wavelength of not less than 400 nanometers and not more than 500 nanometers is absorbed into the mixture. A wavelength of more than 500 nanometers and not more than 800 nanometers travels easily through the mixture.

On the other hand, if the mixture does not contain any one of TMPD, WST-8, and at least one of Cercospora fungus and Pseudocercospora fungus, light having a wavelength of not less than 400 nanometers and not more than 500 nanometers is not absorbed so well into the mixture. A wavelength of more than 500 nanometers and not more than 800 nanometers does not travel easily through the mixture. This difference of the absorbance is reflected in the value of Ay/Ax.

Second Embodiment

The method according to the second embodiment comprises the step (a) and the step (e). The step (a) included in the second embodiment is the same as the step (a) included in the first embodiment.

(Step (e))

As is clear from the inventive examples which will be described later, only if the sample contains at least one of Cercospora fungus and Pseudocercospora fungus, the mixture is orangey. On the other hand, if the sample does not contain either Cercospora fungus or Pseudocercospora fungus, the mixture is purple due to TMPD. Therefore, in the step (e), if the mixture is orangey, it is determined that the sample contains at least one of Cercospora fungus and Pseudocercospora fungus. On the other hand, if the mixture is not orangey, it is determined that the sample does not contain either Cercospora fungus or Pseudocercospora fungus. Easy determination can be conducted visually.

The present inventor believes that the reason why the mixture containing at least one of Cercospora fungus and Pseudocercospora fungus is orangey is that transparent WST-8 is reduced due to Cercospora fungus or Pseudocercospora fungus and is thereby turned into an orangey WST-8 formazan.

The present invention includes a device which is used for conducting the above-mentioned determination method. The device according to the present invention comprises, at least, WST-8 and TMPD.

The device according to the present invention may further comprise a container for containing the sample, a culture for cultivating fungus, a light source capable of emitting light having a predetermined wavelength, an absorption spectrometer for measuring absorbance, an optical sensor for optically detecting the color given to a fungus color reaction reagent, or a display device for displaying a result of detection.

EXAMPLES

Hereinafter, the present invention will be described in more detail with reference to the following examples.

Inventive Example 1

The present inventor cut an agar medium in which fungus of Cercospora sorghi had been incubated over three days with a metal hook. Then, the present inventor added the cut medium to 10% potato dextrose liquid medium (product of Difco Laboratories, hereinafter, referred to as "10% PDB") to provide a mixture. The mixture was stirred with a micropipette. The mixture was filtrated with a cell strainer (purchased from Corning Incorporated, trade name: product #352235). In this way, the agar medium was removed.

The present inventor calculated a concentration of spores contained in the filtrate with a Fuchs-Rosenthal hemocytometer (purchased from Sunlead Glass Corp, trade name: A131). Then, the present inventor diluted the mixture with the 10% PDB on the basis of the concentration of the spores to prepare a sample solution in such a manner that the number of the spores contained in the sample solution was 100,000 per milliliter. The sample solution (170 microliters) was supplied to each of wells of a transparent flat-bottom 96-well microplate. Then, an acetic acid buffer solution (0.1M, pH: 5.5. 20 microliters) was added to each of the wells. Subsequently, a mixture solution (10 microliters) of WST-8 and TMPD was added thereto. Each of the mixture contained in one well had a volume of 200 microliters.

In advance, the present inventor mixed a WST-8 solution (included in a Microbial Viability Assay Kit-WST, purchased from Dojindo Molecular Technologies, Inc.) with a TMPD aqueous solution (10 mM, purchased from Tokyo Chemical Industry Co., Ltd.) at a volume ratio of 9:1 to prepare the mixture solution of WST-8 and TMPD.

The transparent flat-bottom 96-well microplate was left at rest for one day at a temperature of 25 degrees Celsius. The present inventor measured an absorbance of the one well at a wavelength of not less than 400 nanometers and not more than 800 nanometers at 10-nanometer interval with a plate reader (purchased from Tecan Trading AG, trade name:

M1000PRO). The present inventors calculated a ratio of an absorbance Ay at a wavelength of 460 nanometers to an absorbance Ax at a wavelength of 610 nanometers. The calculated ratio was 3.3. The one well was orangey. The inventive example 1 was repeated four times. Table 1 shows the detailed results of the experiments.

Inventive Example 2

In the inventive example 2, an experiment similar to the inventive example 1 was conducted except for using the 10% PDB in place of the acetic acid buffer solution. The mixture solution had a pH of 5.1. The inventive example 2 was repeated four times.

Inventive Example 3

In the inventive example 3, an experiment similar to the inventive example 1 was conducted except for using Cercospora zeae-maydis in place of Cercospora sorghi.

Inventive Example 4

In the inventive example 4, an experiment similar to the inventive example 1 was conducted except for the following three matters (i)-(iii).
(i) Cercospora zeae-maydis was used in place of Cercospora sorghi.
(ii) A buffer solution containing Bis(2-hydroxyethyl)iminotris(hydroxymethyl)methane (CAS No. 6976-37-0, hereinafter referred to as "Bis-Tris") was used in place of the acetic acid buffer solution.
(iii) The buffer solution had a pH of 6.5.

Inventive Example 5

In the inventive example 5, an experiment similar to the inventive example 1 was conducted except for using Pseudocercospora fuligena in place of Cercospora sorghi.

Comparative Example 1

In the comparative example 1, an experiment similar to the inventive example 1 was conducted except that the buffer solution was a HEPES buffer solution having a pH of 7.5 (purchased from Sigma-Aldrich). The pH of the HEPES buffer solution (concentration: 0.1M) was adjusted by using sodium hydroxide.

Comparative Example 2

In the comparative example 2, an experiment similar to the inventive example 1 was conducted except for the following two matters (i)-(ii).
(i) Cercospora zeae-maydis was used in place of Cercospora sorghi.
(ii) The acetic acid buffer solution had a pH of 4.5.

Comparative Examples 3-10

In the comparative examples 3-10, experiments similar to the inventive example 1 were conducted except for using Aspergillus oryzae, Colletotrichum gloeosporioides, Colletotrichum higginsianum, Fusarium avenaceum, Fusarium equiseti, Fusarium oxysporum, Trichoderma harzianum, Penicillium chrysogenum, respectively, in place of Cercospora sorghi. The comparative example 4 was repeated three times.

Comparative Example 11

In the comparative example 11, an experiment similar to the inventive example 1 was conducted except that Cercospora sorghi was not used. The comparative example 11 was repeated three times.

Comparative Examples 12-15

In the comparative examples 12-15, experiments similar to the inventive example 1 were conducted except for the following three matters (i)-(iii).
(i) Colletotrichum higginsianum, Fusarium equiseti, Fusarium oxysporum, and Trichoderma harzianum were used respectively in place of Cercospora sorghi.
(ii) The 10% PDB was used in place of the acetic acid buffer solution.
(iii) The mixture solution had a pH of 5.1.

Comparative Example 16

In the comparative example 16, an experiment similar to the inventive example 1 was conducted except for the following three matters (i)-(iii).
(i) Cercospora sorghi was not used.
(ii) The 10% PDB was used in place of the acetic acid buffer solution.
(iii) The mixture solution had a pH of 5.1.
The comparative example 16 was repeated three times.

Comparative Example 17

In the comparative example 17, an experiment similar to the inventive example 1 was conducted except for the following three matters (i)-(iii).
(i) Fusarium equiseti was used in place of Cercospora sorghi.
(ii) A buffer solution containing Bis-Tris was used in place of the acetic acid buffer solution.
(iii) The buffer solution had a pH of 6.5.

Comparative Example 18

In the comparative example 18, an experiment similar to the inventive example 1 was conducted except for the following three matters (i)-(iii).
(i) Cercospora sorghi was not used.
(ii) A buffer solution containing Bis-Tris was used in place of the acetic acid buffer solution.
(iii) The buffer solution had a pH of 6.5.
The comparative example 18 was repeated three times.

Comparative Example 19

In the comparative example 19, an experiment similar to the inventive example 1 was conducted except for the following three matters (i)-(iii).
(i) Fusarium equiseti was used in place of Cercospora sorghi.
(ii) A HEPES buffer solution was used in place of the acetic acid buffer solution.
(iii) The HEPES buffer solution had a pH of 7.5.

Comparative Example 20

In the comparative example 20, an experiment similar to the inventive example 1 was conducted except for the following three matters (i)-(iii).

(i) Cercospora sorghi was not used.

(ii) A HEPES buffer solution was used in place of the acetic acid buffer solution.

(iii) The HEPES buffer solution had a pH of 7.5.

The following Tables 1-5 show the results of the inventive examples 1-5 and the comparative examples 1-20.

TABLE 1

| | Name of Fungus | Mediator | pH | Buffer solution |
|---|---|---|---|---|
| Inventive Example 1 | Cercospora sorghi | TMPD | 5.5 | Acetic acid buffer solution |
| Inventive Example 2 | Cercospora sorghi | TMPD | 5.1 | None |
| Inventive Example 3 | Cercospora zeae-maydis | TMPD | 5.5 | Acetic acid buffer solution |
| Inventive Example 4 | Cercospora zeae-maydis | TMPD | 6.5 | Bis-Tris |
| Inventive Example 5 | Pseudocercospora fuligena | TMPD | 5.5 | Acetic acid buffer solution |
| Comparative example 1 | Cercospora sorghi | TMPD | 7.5 | HEPES buffer solution |
| Comparative example 2 | Cercospora zeae-maydis | TMPD | 4.5 | Acetic acid buffer solution |
| Comparative example 3 | Aspergillus oryzae | TMPD | 5.5 | Acetic acid buffer solution |
| Comparative example 4 | Colletotrichum gloeosporioides | TMPD | 5.5 | Acetic acid buffer solution |
| Comparative example 5 | Colletotrichum higginisianum | TMPD | 5.5 | Acetic acid buffer solution |
| Comparative example 6 | Fusarium avenaceum | TMPD | 5.5 | Acetic acid buffer solution |
| Comparative example 7 | Fusarium equiseti | TMPD | 5.5 | Acetic acid buffer solution |
| Comparative example 8 | Fusarium oxysporum | TMPD | 5.5 | Acetic acid buffer solution |
| Comparative example 9 | Trichoderma harzianum | TMPD | 5.5 | Acetic acid buffer solution |
| Comparative example 10 | Penicillium chrysogenum | TMPD | 5.5 | Acetic acid buffer solution |

TABLE 2

| | Name of Fungus | Mediator | pH | Buffer solution |
|---|---|---|---|---|
| Comparative example 11 | None | TMPD | 5.5 | Acetic acid buffer solution |
| Comparative example 12 | Colletotrichum higginisianum | TMPD | 5.1 | None |
| Comparative example 13 | Fusarium equiseti | TMPD | 5.1 | None |
| Comparative example 14 | Fusarium oxysporum | TMPD | 5.1 | None |
| Comparative example 15 | Trichoderma harzianum | TMPD | 5.1 | None |
| Comparative example 16 | None | TMPD | 5.1 | None |
| Comparative example 17 | Fusarium equiseti | TMPD | 6.5 | Bis-Tris |
| Comparative example 18 | None | TMPD | 6.5 | Bis-Tris |
| Comparative example 19 | Fusarium equiseti | TMPD | 7.5 | HEPES buffer solution |
| Comparative example 20 | None | TMPD | 7.5 | HEPES buffer solution |

TABLE 3

| | Value of Ay | Value of Ax | Value of Ay/Ax | Liquid color |
|---|---|---|---|---|
| Inventive Example 1 (First) | 0.29 | 0.15 | 1.87 | Orangey |
| Inventive Example 1 (Second) | 0.52 | 0.06 | 8.24 | Orangey |
| Inventive Example 1 (Third) | 0.53 | 0.06 | 8.72 | Orangey |
| Inventive Example 1 (Fourth) | 0.56 | 0.05 | 10.68 | Orangey |
| Inventive Example 2 (First) | 0.27 | 0.11 | 2.36 | Orangey |
| Inventive Example 2 (Second) | 0.47 | 0.13 | 3.69 | Orangey |
| Inventive Example 2 (Third) | 0.48 | 0.11 | 4.51 | Orangey |
| Inventive Example 2 (Fourth) | 0.75 | 0.08 | 9.43 | Orangey |
| Inventive Example 3 | 1.40 | 0.18 | 7.57 | Orangey |
| Inventive Example 4 | 0.76 | 0.18 | 4.14 | Orangey |
| Inventive Example 5 | 2.02 | 0.28 | 7.2 | Orangey |

TABLE 4

| | Value of Ay | Value of Ax | Value of Ay/Ax | Liquid color |
|---|---|---|---|---|
| Comparative example 1 | 0.37 | 0.20 | 1.82 | Orangey |
| Comparative example 2 | 0.14 | 0.16 | 0.91 | Purple |
| Comparative example 3 | 0.20 | 0.26 | 0.78 | Purple |
| Comparative example 4 (First) | 0.19 | 0.28 | 0.66 | Purple |
| Comparative example 4 (Second) | 0.16 | 0.32 | 0.50 | Purple |
| Comparative example 4 (Third) | 0.17 | 0.34 | 0.49 | Purple |
| Comparative example 5 | 0.12 | 0.23 | 0.53 | Purple |
| Comparative example 6 | 0.18 | 0.22 | 0.81 | Purple |
| Comparative example 7 | 0.27 | 0.36 | 0.74 | Purple |
| Comparative example 8 | 0.24 | 0.39 | 0.62 | Purple |
| Comparative example 9 | 0.17 | 0.35 | 0.49 | Purple |
| Comparative example 10 | 0.23 | 0.34 | 0.67 | Purple |

TABLE 5

| | Value of Ay | Value of Ax | Value of Ay/Ax | Liquid color |
|---|---|---|---|---|
| Comparative example 11 (First) | 0.11 | 0.34 | 0.32 | Light purple |
| Comparative example 11 (Second) | 0.10 | 0.34 | 0.31 | Light purple |
| Comparative example 11 (Third) | 0.15 | 0.34 | 0.45 | Light purple |
| Comparative example 12 | 0.13 | 0.19 | 0.65 | Purple |
| Comparative example 13 | 0.30 | 0.29 | 1.04 | Purple |
| Comparative example 14 | 0.25 | 0.24 | 1.01 | Purple |
| Comparative example 15 | 0.19 | 0.27 | 0.71 | Purple |
| Comparative example 16 (First) | 0.10 | 0.26 | 0.39 | Light purple |

TABLE 5-continued

| | Value of Ay | Value of Ax | Value of Ay/Ax | Liquid color |
|---|---|---|---|---|
| Comparative example 16 (Second) | 0.10 | 0.28 | 0.37 | Light purple |
| Comparative example 16 (Third) | 0.15 | 0.29 | 0.52 | Light purple |
| Comparative example 17 | 0.36 | 0.26 | 1.35 | Purple |
| Comparative example 18 (First) | 0.12 | 0.35 | 0.36 | Light purple |
| Comparative example 18 (Second) | 0.17 | 0.35 | 0.48 | Light purple |
| Comparative example 18 (Third) | 0.11 | 0.29 | 0.38 | Light purple |
| Comparative example 19 | 0.71 | 0.29 | 2.44 | Orangey |
| Comparative example 20 | 0.15 | 0.23 | 0.65 | Light purple |

As is clear from the above Tables, if the following requirements (I), (II), and (III) are satisfied, it is selectively determined that the sample contains at least one of Cercospora fungus and Pseudocercospora fungus.

Requirement (I): The aqueous solution contains TMPD.

Requirement (II): The aqueous solution has a pH of not less than 5.1 and not more than 6.5.

Requirement (III): The value of Ay/Ax is not less than 1.5.

As is clear from the comparison of the inventive example 3 with the comparative example 2, in case where the aqueous solution has a pH of 4.5, the value of Ay/Ax is less than 1.5, despite that the sample contains Cercospora fungus and that the aqueous solution contains TMPD. On the other hand, as is clear from the comparison of the inventive examples 2 and 4 with the comparative examples 1 and 19, in case where the aqueous solution has a pH of 7.5, the value of Ay/Ax is not less than 1.5, no matter whether the sample contains Cercospora fungus. In other words, in case where the aqueous solution has a pH of 7.5, the value of Ay/Ax is not less than 1.5, although the sample does not contain Cercospora fungus.

As is clear from the comparison of the inventive examples 1-5 with the comparative examples 2-18 and 20, in case where the sample does not contain Cercospora fungus or Pseudocercospora fungus, the value of Ay/Ax is less than 1.5.

INDUSTRIAL APPLICABILITY

The present invention provides a method for determining whether or not a sample contains at least one of Cercospora fungus and Pseudocercospora fungus.

The invention claimed is:

1. A method for determining selectively whether or not a sample contains at least one selected from the group consisting of Cercospora fungus and Pseudocercospora fungus, the method comprising:
    (a) adding the sample to an aqueous solution containing N,N,N',N'-Tetramethyl-1,4-phenylenediamine and 5-(2,4-disulfophenyl)-3-(2-methoxy-4-nitrophenyl)-2-(4-nitrophenyl)-2H-tetrazolium to provide a mixture, wherein the aqueous solution has a pH of not less than 5.1 and not more than 6.5;
    (b) irradiating the mixture with light having a wavelength of not less than 400 nanometers and not more than 500 nanometers to measure a first absorbance Ay of the mixture;
    (c) irradiating the mixture with light having a wavelength of more than 500 nanometers and not more than 800 nanometers to measure a second absorbance Ax of the mixture; and
    (d) determining that the sample contains the at least one selected from the group consisting of Cercospora fungus and Pseudocercospora fungus, if a mathematical formula Ay /Ax≥1.5 is satisfied.

2. The method according to claim 1, wherein the Cercospora fungus is at least one selected from the group consisting of Cercospora sorghi and Cercospora zeae-maydis.

3. The method according to claim 1, wherein the Pseudocercospora fungus is Pseudocercospora fuligena.

4. The method according to claim 1, wherein the aqueous solution is a buffer solution.

5. A method of determining selectively whether or not a sample contains at least one selected from the group consisting of Cercospora fungus and Pseudocercospora fungus, the method comprising:
    (a) adding the sample to an aqueous solution containing N,N,N',N'-Tetramethyl-1,4-phenylenediamine and 5-(2,4-disulfophenyl)-3-(2-methoxy-4-nitrophenyl)-2-(4-nitrophenyl)-2H-tetrazolium to prepare a mixture, wherein the aqueous solution has a pH of not less then 5.1 and not more the 6.5; and
    (b) determining that the sample contains the at least one selected from the group consisting of Cercospora fungus and Pseudocercospora fungus, if the mixture is orange.

6. The method according to claim 5, wherein the Cercospora fungus is at least one selected from the group of Cercospora sorghi and Cercospora zeae-maydis.

7. The method according to claim 5, wherein the Pseudocercospora fungus is Pseudocercospora fuligena.

8. The method according to claim 5, wherein the aqueous solution is a buffer solution.

* * * * *